Figure 1:
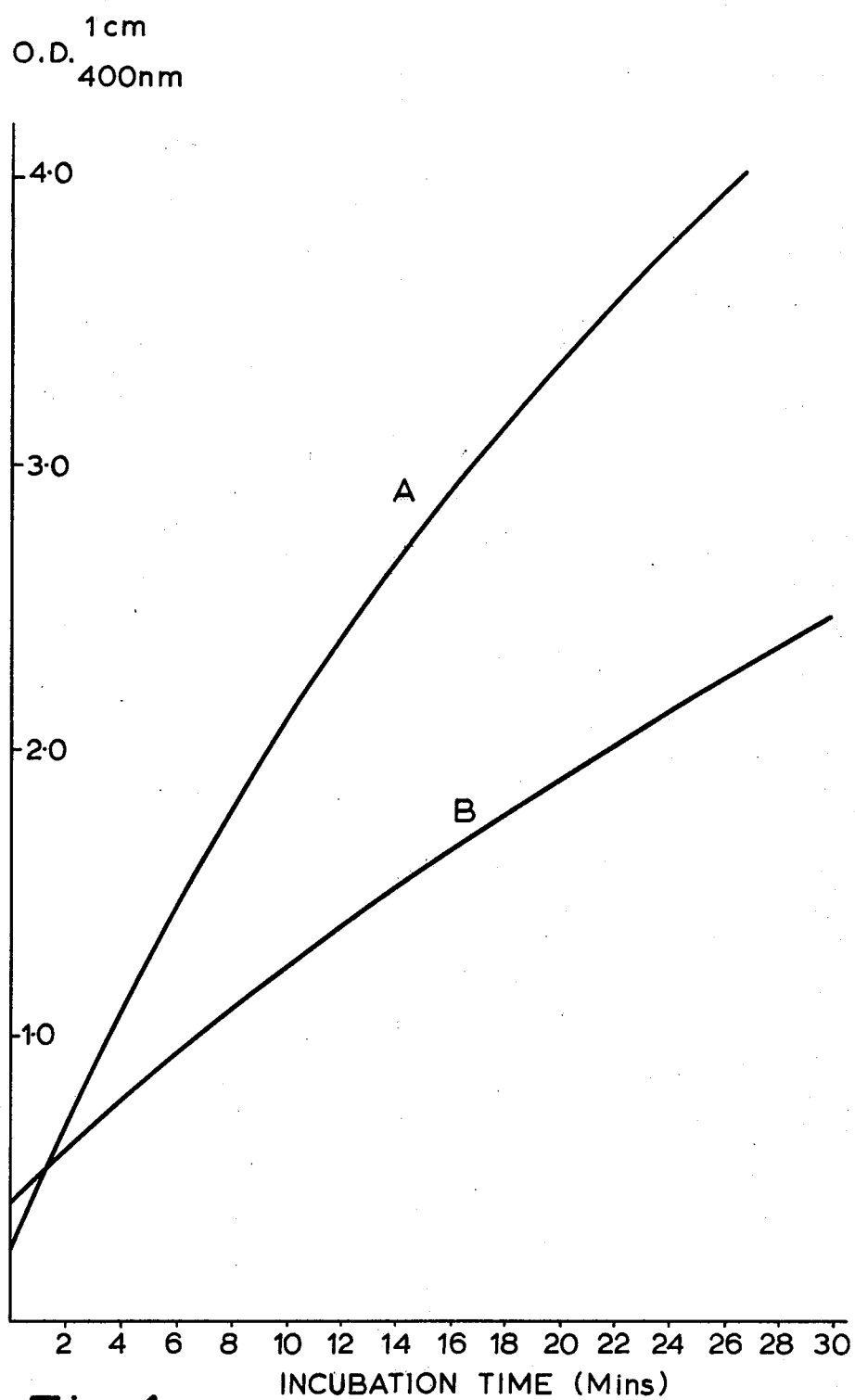

United States Patent [19]

Smith

[11] 4,267,273

[45] May 12, 1981

[54] ENZYME PREPARATION HAVING AFFINITY FOR WATER-IMMISCIBLE LIQUIDS

[75] Inventor: Richard A. G. Smith, Wallington, England

[73] Assignee: Beecham Group Limited, England

[21] Appl. No.: 29,204

[22] Filed: Apr. 12, 1979

Related U.S. Application Data

[63] Continuation of Ser. No. 912,363, Jun. 5, 1978, abandoned, which is a continuation of Ser. No. 769,047, Feb. 16, 1977, abandoned, which is a continuation of Ser. No. 603,148, Aug. 8, 1975, abandoned.

[30] Foreign Application Priority Data

Aug. 13, 1974 [GB] United Kingdom ............... 35556/74
Apr. 26, 1975 [GB] United Kingdom ............... 17434/75

[51] Int. Cl.³ .................... C12P 37/06; C12N 11/00; C12N 11/10
[52] U.S. Cl. ...................................... 435/44; 435/174; 435/177; 435/178; 435/180; 435/181; 435/231; 435/814
[58] Field of Search .................. 435/44, 45, 174, 177, 435/178, 179, 180, 181, 231, 814

[56] References Cited

U.S. PATENT DOCUMENTS

| | | | |
|---|---|---|---|
| 3,706,633 | 12/1972 | Katchalski et al. | 435/178 |
| 3,741,871 | 6/1973 | Weeks et al. | 435/181 X |
| 3,887,432 | 6/1975 | Cawthorne | 435/178 X |

OTHER PUBLICATIONS

Bartling, et al., Synthesis of a Matrix-Supported Enzyme In Non-Aqueous Conditions, Nature, vol. 243, 1973, pp. 342–344.

*Primary Examiner*—David M. Naff

[57] ABSTRACT

An enzyme preparation is prepared having terminal non-polar groups incorporated therein so that the enzyme preparation has affinity for a water-immiscible liquid. The enzyme preparation can be separated from an aqueous reaction mixture by contacting the mixture with the water-immiscible liquid, permitting the enzyme preparation to become associated with the water-immiscible liquid and separating the water-immiscible liquid containing the associated enzyme from the reaction mixture.

27 Claims, 3 Drawing Figures

ENZYME PREPARATION HAVING AFFINITY FOR WATER-IMMISCIBLE LIQUIDS

CROSS-REFERENCE

This is a continuation of Ser. No. 912,363 filed June 5, 1978 which is a continuation of Ser. No. 769,047 filed Feb. 16, 1977 which in turn is a continuation of Ser. No. 603,148 filed Aug. 8, 1975, all now abandoned.

This invention relates to enzyme preparations, and in particular to preparations for effecting chemical transformations, which may be recovered from the reaction medium for re-use.

Enzymatically catalysed transformations are important steps in a large number of chemical processes for example: saponification of lipids using a hydrolase such as lipase; the degradation of protein using a proteolytic enzyme such as trypsin; the production of steroids using a dehydrogenase; the production of glucose syrups from starch using a hydrolase; and the production of 6-amino-penicillanic acid from penicillins such as benzyl-penicillin or phenoxymethylpenicillinic acid using penicillin acylase.

In general, enzymic reactions are carried out with the enzyme in solution in the medium containing the substrate. The expression "substrate" when used in this specification means the substance which the enzyme transforms to give the product. Because the enzyme is dissolved in the reaction medium it is frequently very difficult to separate the enzyme from the substrate or from the product of the transformation when the reaction is complete. Generally, when the product is isolated from the reaction mixture, the separation procedure causes the deactivation of the enzyme. This of course renders the enzyme irrecoverable.

In order to overcome this difficulty of separation and to provide an enzyme system capable of re-use, it is known to attach the enzyme to an insoluble solid support either by adsorption (see for example British Patent Specification No. 1,264,147) or by covalent bonds either directly or indirectly via bridging groups. (See for example British Patent Specifications, 1,349,498, 1,387,460, and 1,365,886. However, such insoluble preparations suffer from a number of disadvantages. Firstly being solids, they are subject to mechanical decay and eventually break up. Secondly the incorporation of enzyme on to the surface of the solid support, and thus the specific activity of the preparation, is often low; and thirdly access of the substrate to the active site of the enzyme is often hindered. Attempts to improve the specific activity of such insoluble enzyme/polymer preparations by increasing the external surface area of the solid, requires a decrease in particle size of the solid preparation, rendering handling and in particular separation by filtration more difficult, and increasing the internal surface area by making the particles more highly porous, produces particles with less mechanical strength.

In addition certain water-soluble enzyme-polymer complexes have been disclosed (see for example British Patent Specification No. 1,284,925 and cognate British patent application Nos. 53822/72 and 44542/73), wherein the enzyme is bound either directly or indirectly via a bridging group to a water soluble polymeric support. These enzyme/polymer complexes are recoverable from the aqueous reaction medium by ultrafiltration. However, ultrafiltration is a difficult and expensive techinique, especially on the large scale and therefore undesirable for industrial applications.

It has now been discovered that certain enzymes may be attached to non-polar groups to render the preparation separable from aqueous media by virtue of the affinity for water-immiscible liquids.

According to this invention there is provided an enzyme preparation comprising an enzyme attached to sufficient non-polar groups, such that on contacting the preparation in aqueous media with an inert water-immiscible liquid, the preparation becomes associated with the inert water-immiscible liquid and is separable thereby from the aqueous medium.

An "inert water-immiscible liquid" as used herein means one which does not react with the enzyme preparation so as to substantially alter the enzymic activity.

The term "associated with" as used above includes any form of interaction between the non-polar groups of the enzyme preparation and the molecules of water-immiscible liquid which is sufficiently stable to provide a means for separation of the enzyme preparation from an aqueous medium.

In general, any enzyme used in a manufacturing process is suitable for incorporation into the preparations of this invention, examples of such enzymes include Amylase, Asparaginase, Neutral and Alkaline Protease, Chymotrypsin, Cellulase, Dextranase, Lipase, Oxynitrilase, Pepsin, Penicillin acylase and Trypsin.

Preferably the enzyme is Lipase, Penicillin acylase or Trypsin.

Suitable non-polar groups which may be attached to the enzyme are hydrocarbyl groups having at least 6 carbon atoms, suitably $C_6$ to $C_{30}$ alkyl groups, for example n-hexyl n-heptyl, n-octyl, n-nonyl, n-decyl, n-dodecyl, n-octadecyl, 4-methylpentyl, 4,4-dimethyl-pentyl, 3-ethylhexyl; $C_6$–$C_{50}$ alkenyl such as undeca-10-enyl, oleyl, linoleyl; $C_6$ to $C_{20}$ cycloalkyl; $C_6$ to $C_{20}$ cycloalkenyl; aryl and substituted aryl groups, for example phenyl optionally substituted by one to three $C_1$ to $C_6$ alkyl groups; and aralkyl, for example benzyl, 2-phenylethyl, 4-phenylbutyl, 2-tolylethyl.

The enzyme may be attached either directly to the non-polar group, or indirectly via a bridging group.

With some enzymes, the attachment of a number of non-polar groups directly to an enzyme molecule produces a change in conformation and a change in the activity of the enzyme. Because of this and on some occasions because of the structure of the enzyme, it is sometimes not possible to attach sufficient non-polar groups to an enzyme to render the preparation separable from aqueous media, without unacceptably reducing the activity of the enzyme.

To overcome this difficulty it is often preferable to produce an enzyme preparation with the enzyme bonded to or adsorbed on a polymeric support, which may then carry non-polar groups instead of or in addition to those on the enzyme itself. This also provides a convenient way of regulating the relative proportions of non-polar groups to enzyme in the preparation. It is also possible, of course, to attach an enzyme carrying sufficient non-polar groups to render it separable from aqueous media, to a polymeric support which may or may not carry further non-polar groups.

In a second aspect, therefore, the invention provides an enzyme preparation as defined above wherein the enzyme is attached to a polymeric support.

Attachment of the enzyme to a polymer as used in this specification includes both covalent bonding to and adsorption on a polymeric support, as long as the adsorption is sufficiently strong to retain the enzyme onto the support when the preparation is associated with the water-immiscible liquid.

The support suitable for use in the aforesaid preparations may be water soluble or insoluble.

When a water-insoluble polymeric material is employed in the preparations of this invention, it is preferably finely divided so as to present a high surface area for the attachment of the enzyme and thus to impart a high specific activity to the preparation.

Suitable water-insoluble materials include cellulose powder and cellulose derivatives such as carboxymethylcellulose ion exchange resins, nylon, high molecular polysaccharides such as agarose and cross-linked dextrans; polysaccharides modified with modifying agents such as epichlorhydrin or modified to incorporate carboxymethyl or aminoethyl groups; polyacrylates and polymethacrylates. Particularly preferred are agarose and macrorecticular crosslinked polyacrylate and polymethacrylate resins.

Suitable water-soluble materials are polymers of natural origin, for example, polysaccharides such as dextran, dextrins or starch, and polymers of natural origin which have been modified such as partially degraded starch or cellulose; polysaccharides, oligosaccarides and saccharides which have been modified with modifying agents such as epichlorhydrin; and cellulose modified so as to incorporate carboxymethyl, or aminoethyl groups.

Of the above mentioned modified saccharides and oligosaccharides, it has been found that copolymers of epichlorhydrin and either lactose, dextrose or sucrose are particularly suitable. A preferred polymer is the sucrose-epichlorhydrin polymer "Ficoll", with molecular weight of about 400,000. The word "Ficoll" is a Registered Trade Mark.

As well as polymers of natural origin it is also possible to use synthetic water-soluble polymers, such as polymers of polyvinylalcohol and copolymers of maleic or acrylic anhydrides with ethylene, styrene, methyl vinyl ether, divinyl ether or vinyl acetate. Such polymers are, for example, described in West German Offenlegungschriften Nos. 1,948,177 and 1,948,298 and in British Patent Specfication Nos. 1,290,701 and 1,223,281.

A suitable class of water-soluble copolymers are the methyl vinyl ether/maleic anhydride copolymers known as "Gantrez AN". (The word "Gantrez AN" is a Registered Trade Mark.)

The enzyme may be attached directly to a polymer containing the non-polar group or alternatively, there may be bonded to the polymeric support bridging groups to which the enzyme may be attached. Suitably the bridging group is $C_2-C_{10}$ aliphatic $\alpha,\omega$-diamine, such as 1,3-diamino-propane or 1,6-diaminohexane. The amino function of the bridging group is attached to the polymer, and the other is free for coupling to the enzyme, for example via a water-soluble dialdehyde such as glyoxal or glutaraldehyde. The use of such bifunctional bridging groups also results in some cross linking between the enzyme/polymer units. The bridging groups may be employed between enzyme/support; enzyme/non-polar group (with or without the additional presence of a support); or support/non-polar group.

The number of non-polar groups which are incorporated in the preparations of this invention depends on a number of factors. Attachment of non-polar groups to the polymer and/or the enzyme establishes a hydrophobic environment in the vicinity of the enzyme. With some enzymes, too high a degree of hydrophobicity results in deactivation of the enzyme due to the concomitant change in conformation.

A balance is required between attachment of the minimum number of non-polar groups necessary in order to permit separation from aqueous media, and the maximum number compatable with the stability of the enzyme. Determination of this balance must perforce remain a matter of routine trial and error. The criteria by which this balance may be determined are as follows:

(1) The molecular weight of the polymeric support.
(2) The molecular weight of the monomer unit.
(3) The percentage of monomer units in the polymer substituted by non-polar groups.
(4) The size of the non-polar groups.
(5) The identity of the enzyme.
(6) The degree of substitution of polymer by the enzyme.

For example, when the support is Gantrez AN 119, (polymer molecular weight 230,000 monomer unit molecular weight 156) where 1 mole of Gantrez AN 119 is substituted by 1 mole of penicillin acylase, the minimum substitution necessary for effective separation from aqueous media occurs when about 25% of the monomer units are substituted by n-decyl groups; and the maximum substitution to retain enzymatic activity occurs when about 50% of the monomer units are substituted by n-octadecyl groups.

The invention also provides a process for producing an enzyme preparation as defined above, which process comprises contacting a compound of formula (I):

$$R-X \qquad (I)$$

wherein R is a non-polar group, and X is a functional group; with an enzyme attached to an active group capable of reacting with the group X.

The group X may be for example an amino, carboxyl, aldehyde, hydroxy, thiol or azo group; or reactive linking groups derived from, for example, dialdehydes such as glyoxal or glyceraldehyde, and/or diamines, such as 1,6-hexamethylene diamine or ethylene diamine, and/or $\alpha,\omega$-aminoaliphatic carboxylic acids such as glycine or 6-aminohexaminoic acid; or a polymeric support material containing any such functional group. Preferably X is an amino group, or a moeity carrying an amino group.

The active group attached to the enzyme and capable of reacting with the group X, may be a group present on the enzyme, either inherently or by modification, such as, for example, carboxyl, amino, thiol or phenolic hydroxy groups, or anhydride linkages; or a polymeric support material containing such an active group; or a reactive linking group such as exemplified with respect to the group X above.

The reaction between the compound of formula (I) and the enzyme is most advantageously carried out at substantially neutral pH, suitably in the range pH4–pH9 and at a temperature in the range $-4°$ C. to $+40°$ C. depending on the enzyme. Preferably the pH is about 7.0 and the temperature in the range 0°–5° C.

When the enzyme preparation consists essentially of the enzyme and non-polar groups alone, it is preferable that the group X is derived from a dialdehyde and/or an $\alpha,\omega$-diamine, that is the non-polar groups are attached to the enzyme via such bridging groups.

In making an enzyme preparation of this invention which also comprises a polymeric support it is preferable that the support should be first modified to incorporate the non-polar group, and where necessary the bridging group, prior to the attachment of the enzyme. In this embodiment the group X in formula (I) above represents a polymeric material bonded to the non-polar group R and to a functional group.

The enzyme/modified polymer preparations may then be prepared by any of the known methods for linking enzymes to polymers. Such linking methods are described, for example in British Pat. No. 1,325,912, and include coupling the enzyme to the polymer by the use of such reagents as cyanogen halides, particularly cyanogen bromide; s-triazines, particularly 2-amino-4, 6-dichloro-s-triazine; acyl-azides, diazonium compounds, for example 2-hydroxy 3-(p-diazophenyl) propyl ether; organic cyanates such as phenyl cyanate; and carbodiimides. Often such linking agents are used first to react with the polymer and provide reactive groups on the same, which groups are then caused to react with the enzyme. In some cases the enzymes may react directly with the polymer, for example if this contains, or has been modified to contain active groups such as anhydride linkages or acidazide groups.

It will be appreciated therefore that the reaction method and conditions employed to produce the modified polymers and to link them to enzymes, will vary according to the nature of the enzyme and of the polymeric material.

For most enzyme/polymer preparations, one convenient procedure is illustrated in scheme I. The first step is to attach to the polymer (a) the non-polar groups preferably via a primary or secondary amine $R.NH_2$ or $R_2.NH$ and (b) bridging groups such as $\alpha,\omega$-diamines for subsequent attachment to enzyme via dialdehyde groups. These reactions are suitably carried out in aqueous solution or suspension at alkaline pH [suitably pH 8-12] and at room temperature. The enzyme carrying dialdehyde groups may then be coupled to the modified polymer in aqueous media at substantially neutral pH.

SCHEME I

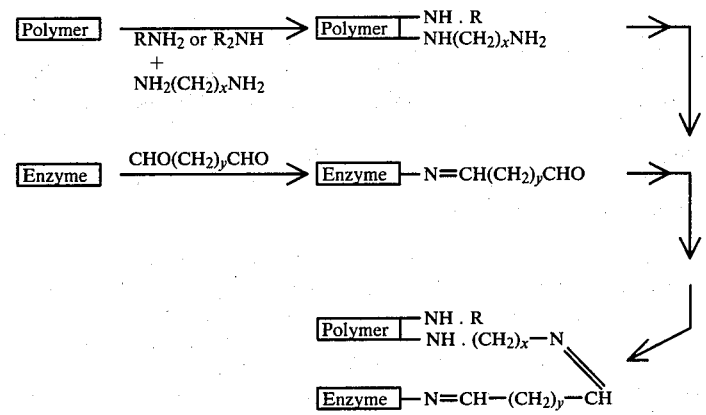

wherein
R is a non-polar group as referred to above;
$NH_2(CH_2)_xNH_2$ represents an $\alpha,\omega$-diamine; and
$CHO(CH_2)_yCHO$ represents a dialdehyde.

It is often necessary to activate groups on the polymer, preferably with cyanogen bromide, before attachment on the non-polar groups is possible.

On the other hand, some polymers have groups present which may be used to couple with non-polar groups and/or enzyme if desired without intermediate bridging groups. Enzyme preparations of the invention prepared in this way then lack the cross-linking associated with the use of bridging groups and often possess advantageous properties as discussed below.

For example, in polymers based on maleic anhydride monomer, such as 'Gantrez' materials, the anhydride groups along the backbone can be used to attach both non-polar groups and enzymes. Suitably the polymer is first modified by attachment of non-polar groups and the remaining anhydride groups in the polymer then used directly to couple with the enzyme. This process is illustrated in scheme II:

SCHEME II

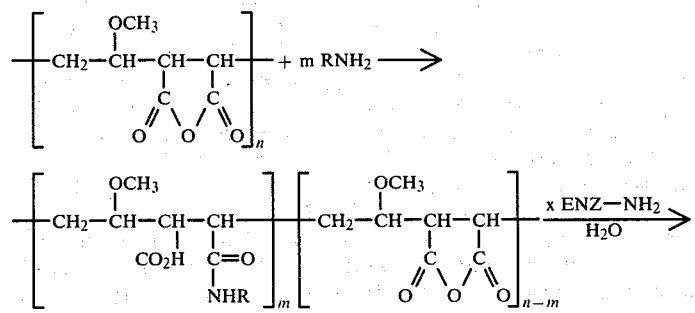

SCHEME II -continued

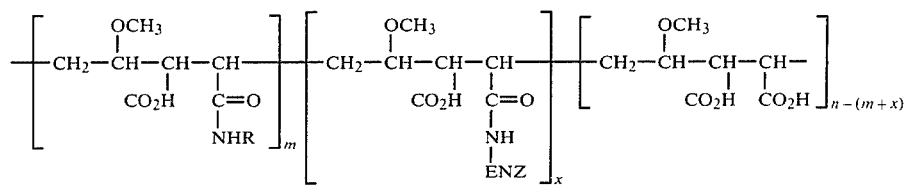

R represents the non-polar group as referred to above; ENZ-NH$_2$ represent the enzyme, carrying an amino group.

Gantrez polymers, for example Gantrez AN119 and Gantrez AN149 have a further advantage in that they dissolve without reaction in certain aprotic non-aqueous solvents, such as dimethylformamide, which are also good solvents for the amines RNH$_2$ and R$_2$NH. A homogenous reaction mixture is possible and therefore such solvents provide advantageous reaction media for the attachment of non-polar groups to these polymers when producing the enzyme preparations of this invention.

Accordingly in a preferred embodiment enzyme/polymer preparations of this invention are prepared by reacting a polymeric material having anhydride groups on the backbone with an amine of formula RNH$_2$ or R$_2$NH in an aprotic non-aqueous polar solvent, wherein R is a non-polar group; and subsequently attaching the modified polymer to an enzyme.

It is preferable that the amine is reacted with the polymer in the presence of tertiary base for example pyridine. The expression "tertiary base" used herein means a tertiary amine or heterocyclic aromatic amine.

Preferably the non-aqueous aprotic solvent is N,N-dimethylformamide, or the tertiary base itself. The temperature at which the reaction is performed is dependent upon the identity of the polymeric support and the amine. However, in general the reaction is carried out at a temperature between room temperature and 100° C.

The modified polymeric support may be isolated from the medium in which it is prepared by precipitation with a less polar solvent, most suitably diethylether or by addition of the solution to water when swelling and anhydride hydrolysis occurs, and isolation of the hydrolysed modified polymer from the aqueous medium using a water immiscible liquid, or by centrifugation.

The enzyme is then attached to the above mentioned isolated modified support by contacting the modified support with the enzyme in aqueous solution, optionally with a coupling agent for example a substituted carbodiimide. Alternatively, the non-hydrolysed reaction mixture, or non-hydrolysed modified polymer dissolved in a small volume of a polar non-aqueous solvent, can be added directly to an aqueous solution of the enzyme.

Alternatively, coupling may be achieved by first adapting the above mentioned non-hydrolysed support by treating it with hydrazine hydrate in dimethylformamide solution. This adapted support, which is then hydrolysed and isolated from aqueous medium by centrifugation, can be coupled with the enzyme in aqueous media using sodium nitrite as an activator.

In a further aspect, the present invention, provides a process for carrying out an enzymic reaction, which process comprises contacting in aqueous medium, an enzyme preparation as defined herein with a substrate for the enzyme; thereafter separating said enzyme preparation from the aqueous reaction mixture by means of contact with a water-immiscible liquid, recovering the reaction product from the aqueous phase; and optionally reusing the separated enzyme preparation by contacting it with further substrate.

A wide variety of water-immiscible liquids may be used to separate the enzyme preparation from the aqueous medium. Suitable liquids include alkanes, such as heptane, octane, nonane, decane, hexadecane, aromatic hydrocarbons, higher aliphatic esters such as glyceryl trioleate and C$_4$-C$_{12}$ aliphatic alcohols such as n-decanol.

Upon contact with such a liquid the enzyme preparation forms a surface layer at the area of contact between the two. In order to maximise this area of contact, the contacting step usually comprises an agitation, for example by stirring or shaking, to break down the water-immiscible liquid into small droplets. Each droplet is then surrounded by enzyme preparation, adhering to its surface.

This contact of enzyme preparation with water-immiscible liquid may be established before, during, or after the enzymic reaction is carried out. Preferably it is established prior to the enzymic reaction by dispersing, by means of agitation, the enzyme preparation with a water-immiscible liquid in an aqueous medium containing the substrate. Thus during the enzymic reaction the preparation is associated with droplets of water-immiscible liquid which is present as an emulsion in aqueous media, and the dispersion is maintained during the reaction by agitation. When separation of the enzyme preparation is required, the agitation is stopped and the phases coalesce.

Alternatively, the enzyme preparation may be present in the aqueous reaction mixture as a solution or a suspension, and contacted with water-immiscible liquid after the reduction, when separation of the enzyme preparation is required.

The nature of the association of enzyme preparation to water-immiscible liquid varies, depending on the polymeric material and/or the non-polar groups incorporated in the enzyme preparation. For example with the enzyme/polymer preparations which have substantial cross-linking, solid aggregates form and these particules adhere to the droplets of water-immiscible liquid. However, with non-cross linked preparations, typified by the 'Gantrez' supported materials described above (and by non-polymer-containing preparations), there is normally no gross adherence of solid to the droplets, and a monolayer of enzyme preparation is formed on the droplets. This is particularly advantageous when the enzyme reaction is carried out after first contacting the enzyme preparation with water-immiscible liquid to produce such a system.

Whatever the nature of the association, the contact between the enzyme preparation and water-immiscible liquid (usually in the form of droplets) enables separation of the enzyme preparation from aqueous medium. The droplets, coated with enzyme preparation, have approximately the same density as that of the water-immiscible liquid. On allowing to stand the droplets either float on the surface of the aqueous medium (for liquids less dense than water) or settle to the bottom (for more dense liquids). Thus a separate layer is produced comprising water-immiscible liquid associated with enzyme preparation, which is readily recovered from the aqueous medium.

For liquids which do not float on, or settle from, aqueous media sufficiently rapidly, other means of separation may be employed for example centrifugation, or by passing the mixture through a water-repellant filter 15 whereupon the aqueous medium passes through and the water immiscible liquid (together with the enzyme preparation) remains behind and is thereby separated. A preferred enzymic process of this invention is the preparation of 6-aminopenicillanic acid from a penicillin using a preparation based on a penicillin acylase enzyme. In this case preferably the acylase enzyme is obtained from bacteria, such as strains of *Escherichia coli*, when used for the splitting of benzylpenicillin; or fungi of *actinomycetes* when used for the splitting of phenoxymethylpenicillin. Such enzymes are in general well-known. They are used in the production of 6-APA within the pH range of 6.0 to 9.0, preferably at pH 7.0 to 8.5. Since deacylation of a penicillin results in liberation of a free acid from the penicillin side chain, it is necessary to maintain the above-mentioned pH range during the process for preparing 6-APA by the addition as necessary of an alkali, such as solution of sodium or ammonium hydroxide or triethylamine.

Figure 3:
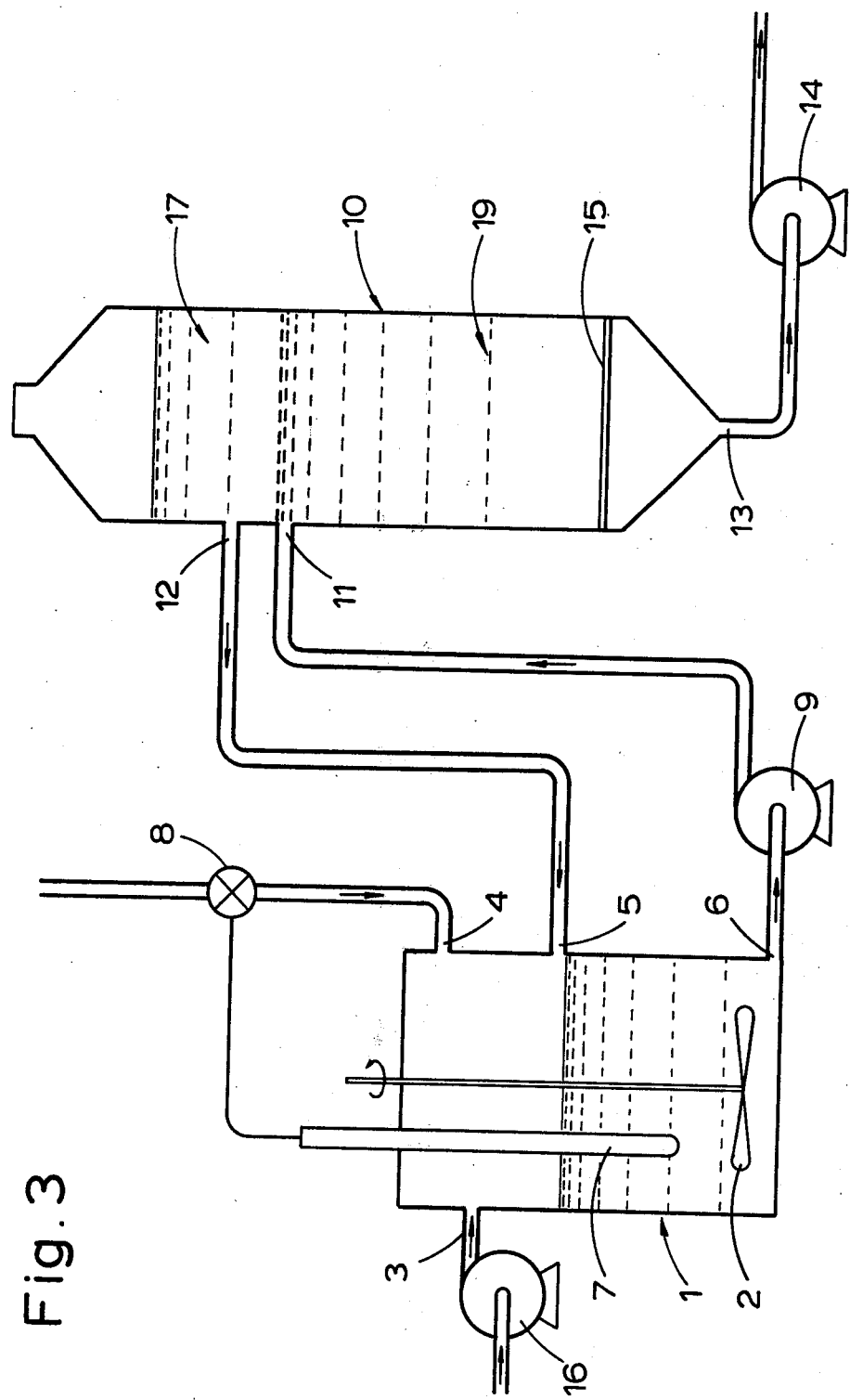

A particular advantage of the use of the enzyme preparations of this invention is the ready application to a continuous method of enzymatic reaction which may be carried out in an apparatus shown in the accompanying FIG. 3, which is a schematic diagram of a suitable reactor.

Referring to FIG. 3, a reactor tank 1 is provided with means for agitation in the form of a stirrer 2, inlets 3, 4 and 5 for substrate, alkali, and enzyme phase respectively, and an outlet 6. The tank 1 also contains a pH-detecting probe 7 which controls a valve 8 connected to the alkali inlet 4. The tank outlet 6 feeds, via a pump 9, a separating vessel 10 through an inlet 11. The separating vessel has an upper outlet 12 connected to reactor tank inlet 5, a lower outlet 13 to remove reaction product via pump 14 and a filter in the form of a glass sinter 15 positioned above the lower outlet 13. The substrate inlet 3 is fed from a pump 16 and pumps 14 and 16 linked to operate at the same flow-rate.

In operation, the reactor tank 1 is charged through inlet 3 with the substrate in aqueous medium together with an enzyme preparation of the invention and a water-immiscible liquid. The mixture is dispersed by the stirrer 2 to produce an emulsion. The tank 1 may be maintained at a constant temperature for example by means of a water jacket (not shown) surrounding the tank. Alkali is added to the emulsion in the tank through the inlet 4 and the rate of such addition is governed by the valve 8 controlled by the probe 7 so that the pH of the reaction mixture is maintained in a range required for optimum reaction. During the course of the reaction, the pump 9 is operated and the mixture is withdrawn from outlet 6 and transferred to the separation vessel 10 through inlet 11. In vessel 10 the water-immiscible liquid (in this case less dense than water) forms a separate upper layer 17 carrying with it the enzyme preparation. The lower aqueous layer 18 containing reaction product is withdrawn through the filter 15 and thence through outlet 13 by means of the pump 14. The upper layer 17 containing enzyme preparation associated with water-immiscible liquid is allowed to flow through outlet 12 and returned to the reactor tank 1 through inlet 5. As the product is withdrawn through outlet 13, further substrate solution is added to the tank 1 through the inlet 3 by means of the pump 16. The pumps 14 and 16 are co-ordinated so that the rate of input of substrate is equal to the rate of outflow of product.

The rates of flow, the residence time in the reactor tank and other parameters of the reaction will depend on the particular enzyme preparation/substrate system concerned. From preliminary results it can be shown that a 10,000-liter reactor using 1,000 kg. of an enzyme preparation based on penicillin acylase attached to a Gantrez AN149 support could process about 2,000 kg. of penicillin G per day at a concentration of 5% w/v at 22° C. and pH 7.8, although this figure could be improved with enzyme preparations of higher specific activity.

The following examples illustrate the production and properties of some of the enzyme polymer complexes of this invention.

In the examples, the following abbreviations are employed to designate the polymers and modified polymers, enzymes, linking groups, non-polar groups and coupling agents:

Enzymes:
 L:Lipase
 PA:Penicillin Acylase
 T:Trypsin
Supports:
 F:Ficoll
 GAN:Gantrez
 SR:Sepharose
 T2000:Dextran T.2000
Enzyme/Support Linkage Group:
 HD:1,6-diaminohexane
Non-polar groups:
 D:n-decylamino
 DD:n-dodecylamino
 OD:n-octadecylamino
Linking Agents and Activating Agents and activated Groups:
 CMC:1-Cyclohexyl-3-(2-morpholinoethyl)-carbodiimidemethano-p-toluenesulphonate
 G:Glutaraldehyde
 A-Hydrazide The integer following the notation represents the batch number.

For example, the enzyme preparation of Example 1 is designated PAFHDDG. The enzyme is thus penicillin acylase (PA). The support is Ficoll (F) carrying hexamethylene diamine groups (HD) for attachment to enzyme and also decyl groups (D) as non-polar groups. The coupling between the free amino group of the hexamethylendiamine linkage and the enzyme is carried out using glutaraldehyde (G).

Also GAN 149 HDOD is the modified support prepared from Gantrez 149 modified with 1,6-diaminohexane and octadecylamine and PAGAN 149 HDOD-G, is the modified support above to which is attached penicillin acylase in the presence of glutaraldehyde.

EXAMPLE 1

(a) n-Decylamino, (6-aminohexylamino)-Ficoll(FHDD-1)

Ficoll (5 g) was dissolved in water (300 mls) and adjusted to pH 11.0. Cyanogen bromide (1 g) was added and the pH maintained during reaction, with 2 N NaOH. Reaction ceased after 20 mins. at room temperature and n-decylamine (4 g) and 1,6 diaminohexane (0.5 g) dissolved in methanol (10 ml) were added. The pH was adjusted to 9.5 with 2 N HCl and the mixture stirred for 16 hours at 4° C. The resulting colloidal solution was centrifuged at 22,000 g/1 hours to give a white pellet (35 g wet weight) which was retained and a cloudy supernatant which was discarded.

(b) Penicillin Acylase [n-decylamino, (6-aminohexylamino)-Ficoll](PAFHDDG-1)

FHDD-1 (21.6 g wet weight) was mixed with 0.1 M sodium phosphate buffer pH 6.0 (20 ml) and adjusted to pH 6.2 with 2 N HCl. A solution of *E. coli.* penicillin acylase (50 ml, 340 mg protein partially purified) was adjusted to pH 6.2 at 0° C. and glutaraldehyde (5 ml, 25% w/v aqueous solution) added. After stirring at 0° C. for 30 mins. the FHDD-1 suspension was added. The mixture was stirred at 0° C. for 3 hours and at 4° C. for 4 hours, then frozen (−20° C.) for 16 hours. After thawing, the suspension was centrifuged at 20,000 g/4° C./45 mins. to give a brown gel-like pellet. The gel was resuspended in 0.1 M sodium phosphate buffer pH 7.0 (30 ml) and re-centrifuged at 20,000 g/4° C./30 mins. The supernatents were combined and the brown pellet (approx. 6.3 wet weight) suspended in 0.1 M sodium phosphate buffer pH 7.0 and stored at 4° C. The pellet suspension, when mixed with at least its own weight of n-decanol, floats with the decanol to the surface of aqueous solutions leaving an infranatent free of particulate enzyme. Enzymic activities of pellet, supernatent and stock enzyme are shown in Table 1. Approximately 43% of the initial enzyme activity is recovered, virtually all of it in the conjugate. The activity of the complex can be recovered substantially from penicillin solutions by either floatation or conventional centrifugation.

TABLE 1

Penicillin acylase activity of PAFHDDG

Assay procedure: Penicillin G (sodium salt) is dissolved at the appropriate concentration in 20 ml 0.02M sodium phosphate buffer pH 7.8 at 37° C. and the enzyme sample added. The pH is maintained by the addition of 0.1N or 0.5N NaOH and the activity is expressed as the initial rate of production of 6-aminopenicillanic acid (6-APA). In re-assay procedure 1, 2 ml of n-decanol is added to the stirred reaction mixture and, after the determination, the suspension is allowed to separate into two layers. The upper layer is removed with a syringe and re-used. In procedure 2, the final suspension is centrifuged at 2,000g/15 mins. and the pellet re-used.

| Material | Amount | % w/v Penicillin G in assay | Initial rate 6-APA production moles/min. $\times 10^{-4}$ |
|---|---|---|---|
| Stock enzyme PAFHDDG-1 | 1 ml | 5 | 0.885 |
| Supernatent PAFHDDG-1 | 1 ml | 5 | 0.008 |
| PAFHDDG-1 | 0.5g | 5 | 1.500 |
| PAFHDDG-1 Re-assays | | | |
| Procedure 1. 1. | 0.5g | 5 | 0.860 |
| 2. | 0.5g | 5 | 0.550 |
| 3. | 0.5g | 5 | 0.500 |
| Procedure 2. 1. | 0.5g | 5 | 1.300 |

TABLE 1-continued

Penicillin acylase activity of PAFHDDG

| | | | |
|---|---|---|---|
| 2. | 0.5g | 5 | 1.210 |
| 3. | 0.5g | 5 | 1.110 |
| 4. | 0.5g | 5 | 1.030 |

EXAMPLE 2

(a) n-Octadecylamino, (6-aminohexylamino)-Ficoll (FODHD-1)

Ficoll (5 g) was dissolved in water (300 mls) and the solution treated with cyanogen bromide (1 g) at pH 11.0 as above. After 20 mins. the solution was adjusted to pH 10.0 with 2 N HCl and a solution of n-octadecylamine (5 g) and 1,6 diaminohexane (0.5 g) in methanol (20 ml) added. The pH was re-adjusted to 10.0 with 2 N HCl and the mixture stirred at 4° C. for 72 hours. The product was centrifuged at 20,000 g/ 4° C./45 mins. A loose white pellet (25 ml, retained) and a clear supernatent with a surface scum (octadecylamine) were formed.

(b) Penicillin acylase [n-octadecylamino, (6-aminohexylamino) -Ficoll](PAFODHDG-1)

Penicillin acylase (25 ml, 170 mg protein) was adjusted to pH 6.2 at room temperature and glutaraldehyde (2.5 ml, 25% w/v) added. The mixture was stirred at room temperature for 15 mins., FODHD-1 (10 ml) added and the suspension adjusted to pH 6.2 with 2 N HCl. After stirring at 4° C. for 3 hours, the material was centrifuged at 20,000 g/4° C./30 mins. The pink pellet was re-suspended in 0.1 M sodium phosphate buffer pH 7.0 and stored at 4° C. The suspension is efficiently floated by n-decanol, its activity is shown in Table 2. Recovery of activity was approximately 60%.

TABLE 2

Activity of PAFODHDG-1

Assay procedure: As for Table 1. 5% w/v penicillin G used throughout.

| Material | Amount | Initial rate of 6-APA production moles/min $\times 10^{3\ 4}$ |
|---|---|---|
| Stock enzyme | 1 ml | 0.885 |
| PAFODHDG-1 | 0.5g | 0.940 |
| Re-assays (Procedure 2) | | |
| 1. | 0.5g | 0.800 |
| 2. | 0.5g | 0.585 |

EXAMPLE 3

(a) n-Decylamino, (6-aminohexylamino)-Dextran T2000 (T2000HDD-1)

Dextran (average molecular weight 2,000,000), (10 g) was dissolved in water (800 ml) and activated with cyanogen bromide (2.5 g) as described above. After 20 mins. n-decylamino (5 g) and 1,6 diaminohexane (1.0 g) were added and the pH adjusted to 10.0. The solution was stirred at 4° C. for 16 hours and then centrifuged at 20,000 g/4° C./1½ hours. The pellet formed was resuspended in 0.1 N HCl (100 ml) and centrifuged again (20,000 g/1 hour). The second pellet (C. 50 g wet weight) was retained.

(b) Penicillin acylase [n-decylamino, (6-aminohexylamino)-Dextran T2000] Pat2000HDDG-1

T2000HDD-1 (10 g wet weight) was homogenised in 0.1 M sodium phosphate buffer pH 6.0 and the suspension adjusted to pH 6.2. Penicillin acylase (50 ml 340 mg protein) was adjusted to pH 6.2 and glutaraldehyde (5 ml, 25% w/v) added. This solution was stirred for 45 mins. at 4° C. and then the T2000HDD added. The mixture was stirred at 4° C. for 30 mins. and then stored at −20° C. for 16 hours. After thawing, the suspension was stirred at room temperature for 1 hour and then centrifuged, (6,000 g/22° C./30 mins.). The supernatent was retained and the pellet re-suspended in 0.1 M sodium phosphate pH 7.0 (75 ml) and homogenised. Centrifugation as before, followed by re-suspension and further centrifugation gave a brown pellet (8.0 g wet weight). This is efficiently floated by n-decanol and, less efficiently, by n-heptane. The activity of this preparation is given in Table 3. Approximately 10% of the original enzyme activity was present in the conjugate.

TABLE 3

Activity of PAT2000HDDG-1

Assay procedure: As before, 5% w/v penicillin G used throughout.

| Material | Amount | Initial rate of 6-APA Production moles/min × 10$^{-4}$ |
|---|---|---|
| Stock enzyme PAT2000HDDG-1 | 1 ml | 0.875 |
| Supernatent | 1 ml | 0.022 |
| PAT2000HDDG-1 | 0.5g | 0.270 |
| Re-assay (Procedure 2) | 0.5g | 0.155 |

EXAMPLE 4

(a) n-Decylamino, (6-aminohexylamino) Sepharose 4B (SRHDD-1)

Cyanogen bromide-activated Sepharose 4B (2 g dry weight) was swollen in 50 ml $10^{-3}$ N HCl at 4° C. for 15 mins. and then washed on a glass sinter with 2×100 ml $10^{-3}$ N HCl. The gel was added to a solution of 0.1 M sodium bicarbonate (20 ml), ethanol (5 ml), n-decylamino (0.5 g) and 1,6 diaminohexane (0.1 g). The mixture was rotated slowly at 4° C. for 16 hours and then filtered on a glass sinter. The gel was washed under suction with 4×20 ml $10^{-3}$ N HCl, 4×20 ml ethanol and 4×50 ml water and then resuspended in water and stored at 4° C.

(b) Penicillin acylase [n-decylamino, (6-aminohexylamino)-Sepharose 4B] PASRHDDG-1

Suction dried SRHDD-1 gel (1.5 g) was suspended in 0.1 M sodium phosphate buffer pH 6.0 (5 ml) and glutaraldehyde (0.5 ml, 25% w/v) added. The mixture was agitated for 2 hours at room temperature and then suction dried on a glass sinter. The gel was then added to a mixture of penicillin acylase (2 ml, 13.6 mg) and 0.1 M sodium phosphate buffer pH 6.0 (3 ml). This mixture was agitated for 24 hours at 4° C. sucked dry and washed on the sinter with 5×20 ml 0.1 M sodium phosphate buffer pH 7.0. It was suspended in 5 ml of the same buffer. The resulting beads are floated with n-decanol in contrast to unmodified Sepharose which sediments from aqueous suspensions containing n-decanol. The activity of this preparation is shown in Table 4. Approximately 72% of the original activity is present in the conjugate.

TABLE 4

Penicillin acylase activity of PASRHDDG-1

Assay procedure: As before, 5% w/v penicillin G used throughout.

| Material | Amount | Initial rate of 6-APA Production moles/min × 10$^{-4}$ |
|---|---|---|
| Stock enzyme | 1 ml | 0.885 |
| PASRHDDG-1 | 2 ml | 0.505 |
| Re-assays Procedure 2. 1. | 2 ml | 0.410 |
| 2. | 2 ml | 0.375 |

TABLE 4-continued

Penicillin acylase activity of PASRHDDG-1

Assay procedure: As before, 5% w/v penicillin G used throughout.

| Material | Amount | Initial rate of 6-APA Production moles/min × 10$^{-4}$ |
|---|---|---|
| Procedure 1. 3. | 2 ml | 0.270 |

EXAMPLE 5 n-Decylaminoglutaral-Penicillin acylase (PADDG-1)

Penicillin acylase (40 ml, 272 mg) was adjusted to pH 6.2 and glutaraldehyde (4 ml, 25% w/v) added. After stirring for 20 mins. at 0° C., n-decanol (6 ml) and n-decylamine (0.6 ml) were added and vigorous stirring continued at 0° C. for 6 hours and at room temperature for 1 hour. The mixture was centrifuged at 2,000 g/22° C./10 mins. to give a brown supernatent layer which was removed and stored suspended in 0.1 M sodium phosphate buffer pH 7.0 (30 ml). The material floats spontaneously to the surface of aqueous suspensions but is somewhat less dispersable than the polymer conjugates, and has a tendency to form large aggregates. 1 ml of the suspension, assayed as in Example 1, showed an activity of $0.49 \times 10^{-4}$ moles/min which represents 42% retention of acylase activity in the conjugate.

EXAMPLE 6

Trypsin-[n-octadecylamino, (6-aminohexylamino)-Ficoll] (TFODHDG-1)

Trypsin (50 mg, salt-free) was dissolved in 0.1 M sodium phosphate buffer pH 6.0 (20 ml) at 0° C. Glutaraldehyde (1 ml, 25% w/v) was added and the mixture stirred for 15 mins. at 0° C. FODHD-1 (10 ml), Ex 2a, was added and the solution adjusted to pH 6.2 with 2 N HCl. The mixture was stirred for 16 hours at 4° C. and then centrifuged 20,000 g/4° C./30 mins. The pellet was re-suspended in 20 ml water and filtered using Whatman IPS phase-separating papers. The residue was re-suspended in $10^{-3}$ M HCl (20 ml) and re-filtered. Re-suspension ($10^{-3}$ M HCl) and centrifugation (10,000 g/14° C./20 mins.) were then carried out twice and gave 2.65 g of a brown gel. This material is floatable with both n-decanol and n-heptane. The activity of the conjugate is shown in FIG. 1. The assay procedure was as follows:

N-α-Benzoyl-DL-arginine-p-nitroanilide was dissolved in dimethylformamide (5 ml) and added to 0.05 M Tris. buffer pH 8.3 (containing 10 mM $CaCl_2$) (45 ml) to give a $2 \times 10^{-3}$ M solution of the chromogenic substrate. n-Heptane (5 ml) was added and the mixture vigorously stirred at 22° C. The enzyme sample was added and 5 ml aliquots of mixture removed at intervals. On standing briefly, or centrifuging gently, the heptane layer separated (taking with it the TFODHDG-1). The lower aqueous layer was removed and O,D$_{400nm}$ taken to determine release of p-nitroanilide. Droplets of heptane give a significant 'blank' absorbance value. In some cases the lower layer was diluted to facilitate absorbance readings. After reading, both heptane and aqueous layers were returned to the stirred reaction mixture. The total activity retained by the conjugate was 17% of the original amidolytic activity.

EXAMPLE 7

Lipase-[n-decylamino, (6-aminohexylamino)-Dextran T2000] (LT2000HDDG-1)

Figure 2:
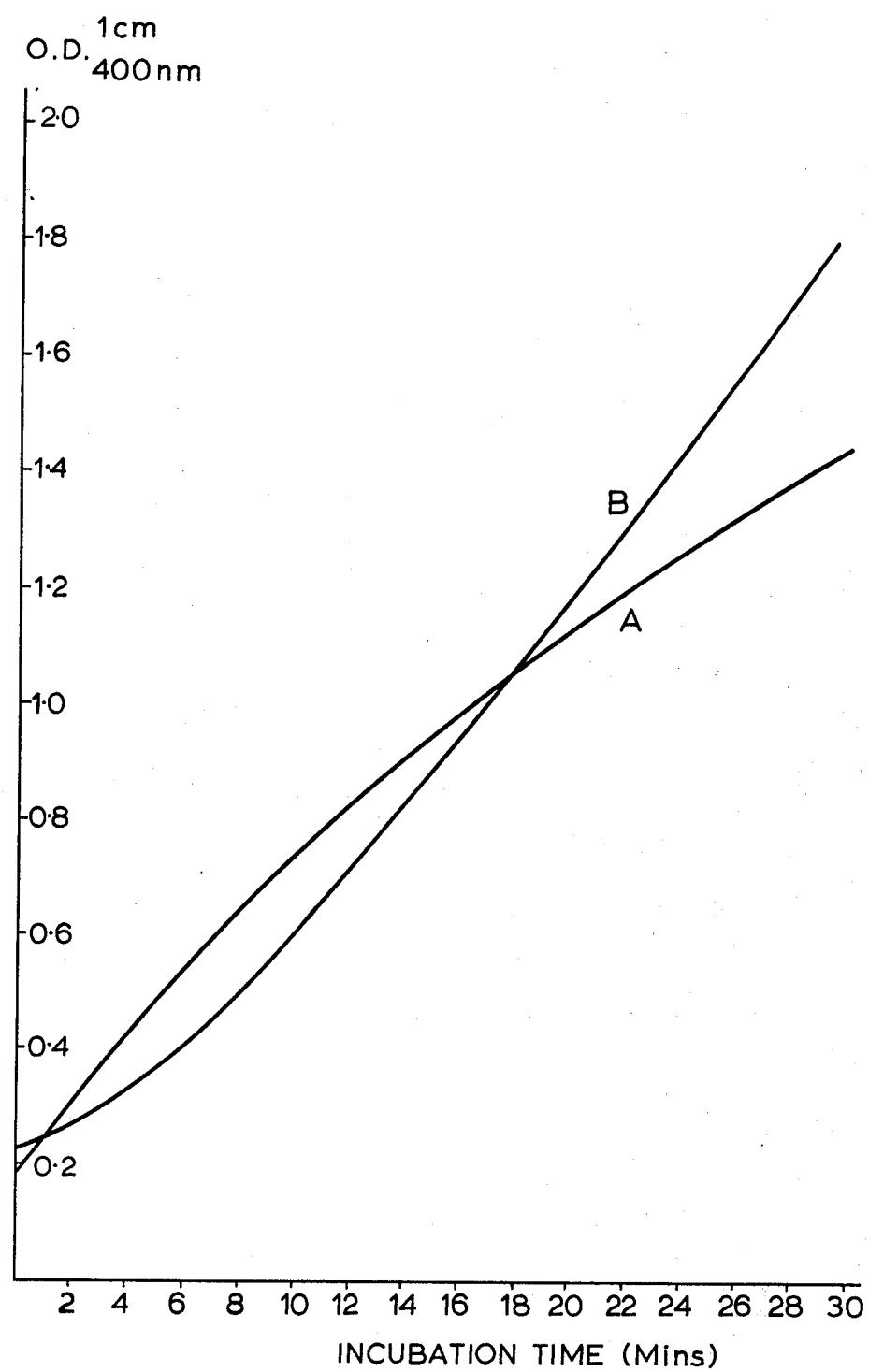

Candida Cylindracea Lipase (200 mg) was dissolved in 0.1 M Sodium phosphate pH 6.0 (20 ml) and adjusted to pH 6.2 Glutaraldehyde (2 ml, 23% w/v) was added and the mixture stirred for 30 mins. at room temperature. T2000HDD-1 (Ex3) was precipitated from suspension with ethanol and the precipitate re-swollen in water. 10 g of the resulting gel was homogenised in 0.1 M sodium phosphate pH 6.0 (20 ml) and added to the enzyme-glutaraldehyde mixture. The pH was adjusted to 6.2 and the mixture stirred at 4° C. for 16 hours. The suspension was centrifuged 20,000 g/4° C./30 mins. and the pellet re-suspended in 0.1 M sodium phosphate pH 7.0 (50 ml) and recentrifuged. This procedure was repeated two more times. The final pellet (8.4 g wet weight) was re-suspended in 20 ml 0.1 M sodium phosphate pH 7.0. The suspension is floatable with both n-decanol and n-heptane. The activity of the conjugate is shown in FIG. 2. The assay procedure was as follows:

p-Nitrophenyl laurate ($10^{-2}$ M in n-heptane), 5 ml, was stirred rapidly with 0.1 M sodium phosphate pH 8.0 (20 ml) at room temperature. Under these conditions, non-enzymic ester hydrolysis is undetectable over 1 hour or more. After addition of the enzyme, 5 ml aliquots were removed at intervals, centrifuged 4,000/1½ mins. and the lower (aqueous) layer removed. $O.D._{400}$ $nm^1$ $cm$ was determined exactly 3 mins. after removal of the original aliquot. Aqueous and heptane layers were then returned to the stirred mixture. (Since the substrate is in the non-aqueous phase in this experiment, the rate of stirring, i.e. extent of dispersion, should be kept constant throughout the experiment.)

Approximately 1% of the original lipase activity was incorporated into the conjugate.

EXAMPLE 8

(a) GAN149HDOD-1 n-Octadecylamine (1 g) and 1,6 diaminohexane (0.2 g) were suspended in methanol (10 ml) and added to 0.2 M sodium phosphate buffer pH 8.0 (200 ml) containing methanol (40 ml). GANTREZ 149 (2 g) was added in small amounts with vigorous stirring. The mixture was stirred for 16 hours at room temperature and then centrifuged at 12,000 g for 1 hour at room temperature. Scum and supernatent were discarded and the pellet resuspended in 0.1 M sodium phosphate buffer pH 7.0 (100 ml) and re-centrifuged as above. The gel-like pellet (80 g) was stored at 4° C.

(b) PAGAN149HDOD-1-G

Penicillin acylase solution (20 ml $1.36 \times 10^{-7}$ units, 136 mg protein) was adjusted to pH 6.2 and glutaraldehyde (2 ml of 25% w/v in water) added. The mixture was stirred at room temperature and a suspension of GAN149HDOD-1 (10 g) in 0.1 M sodium phosphate buffer pH 6.0 (12 ml) added. pH was maintained at 6.2 and stirring continued at room temperature for 2 hours. The suspension was centrifuged for 1 hour at 20,000 g and 4° C. and the pellet (14 g) retained. The pellet was resuspended in 0.1 M sodium phosphate pH 7.0 (10 ml) and the centrifugation repeated. The final pellet was stored at 4° C.

Specific activity: $3 \times 10^{-5}$ moles 6-APA $\min^{-1}$ (5% penicillin G, pH 7.8 22° C.) Activity recovery: 21%.

Floatable with n-decanol or n-decane.

EXAMPLE 9

(a) GAN149HDOD-2 n-Octadecylamine (5 g) was dissolved in ethanol (50 ml) and added to 0.1 M sodium phosphate buffer pH 9.0 (1 liter) containing ethanol (200 ml). GANTREZ 149 (5 g) was added in small amounts over three-quarters of an hour with stirring. The pH was maintained between 8 and 9 with 2 N NaOH. After Gantrez addition, 1,6-diaminohexane (5 g) was added and the mixture stirred at room temperature for 6 hours. The pH was lowered to 3.0 with conc. HCl and the suspension contrifuged 12,000 g for 1 hour at room temperature. The supernatent was discarded and the pellet resuspended in water (550 ml) and re-centrifuged to give a final white pellet (150 g) which was stored at 4° C.

(b) PAGAN149HDOD-2-G

Penicillin acylase solution (100 ml, $9.8 \times 10^6$ units, 88 mg protein) was mixed with GAN149HDOD-2 (15 g), 0.1 M sodium phosphate buffer pH 6.0 (20 ml) and 2% w/v sodium azide (1 ml); and homogenised briefly at 0° C. The mixture was adjusted to pH 6.8 at 0° C. for 4½ hours and then centrifuged 20,000 g/4° C./1 hour. The pellet was resuspended in 0.1 M sodium phosphate pH 7.0 and re-centrifuged. These operations were then repeated to give a final pellet; wt. 11.2 g, stored at 4° C. Specific activity: $1.8 \times 10^{-5}$ moles 6-APA $\min^{-1} gm^{-1}$. (Conditions as above)

Activity recovery: 55%. Floatable with n-decanol or n-decane.

EXAMPLE 10

Trypsin (n-decylamino Gantrez AN 119)(TGAN 119D)

Gantrez AN 119 (1 g) was dissolved in dimethylformamide (DMF) (5 ml) and vigorously stirred. n-Decylamine (0.3 g) in DMF (1 ml) was added and the solution became more viscous. After stirring for 10 mins. the solution was added dropwise to a solution of bovine trypsin (300 ml) in 0.1 M sodium phosphate buffer pH 8.0 (60 ml) at 22° C. The pH was maintained with 2 N sodium hydroxide, and when no further change occurred sodium chloride (4 g) was added. The resulting suspension was poured into 0.1 M sodium phosphate buffer pH 7.6 (175 ml) and was cooled to 4° C. Ammonium sulphate (50 g) was added and the mixture stirred at 4° C. for 20 mins. The mixture was centrifuged at 25,000 g/4° C./1 hour and the gel-like pellet re-homogenised in 0.1 M sodium phosphate buffer pH 7.6 (30 ml). Centrifugation was repeated, followed by two more homogenisation/centrifugation cycles to give a final loose gel (7.5 g). The preparation was assayed spectrophotometrically using N-Benzoyl-L-Arginine p-Nitroanilide (BANA), 2 mM in 0.1 M veronal buffer pH 8.3 at 22° C. One unit is an increase in optical density of 0.001 per minutes at 400 nm. Since the gel causes appreciable light scattering, it is necessary to shake the cuvette (1 cm path length) intermittently.

Gel activity: 168 units/mg wet weight, 2000 units/mg dry weight (lyophilised gel).

Activity recovery: 24.2%.

The immobilisation of the enzyme conjugate on solvent droplets is illustrated by the following experiment:

Gel (1 g wet weight) was homogenised in a small tissue grinder with n-decane (2.5 ml) and 0.1 M sodium phosphate buffer pH 8.0 (10 ml) at 4,000 r.p.m. and 0° C. for 5 min. The milky suspension separated into an upper layer consisting of close packed decane droplets and a lower aqueous layer over 3 hours at 0° C. Both layers were assayed using the above spectrophotometric method. Again the cuvette was shaken at regular intervals when the upper layer was assayed and the mean rate of optical density increases measured.

Activity of upper phase: 2280 units/ml

Activity of lower phase: 57 units/ml

Since the apparent activity of the upper phase is probably much less than the real activity due to the method, this result indicates that at least 90% of the tryptic activity is associated with the solvent droplets.

EXAMPLE 11

Penicillin Acylase (n-Octadecylamino Gantrez AN 119)(PAGAN119OD)

Gantrez AN 119 (0.5 g) was dissolved in dimethylformamide (2.5 ml) and warmed to 80° C. on a water bath. Octadecylamine (0.28 g) was also dissolved in dimethylformamide (2.5 ml) at 80° C. and added quickly to the Gantrez solution while still hot. The mixture was stirred and pyridine (0.1 ml) added. After cooling to room temperature over 1 hour, the whole solution was added to penicillin acylase (175 mg) in water (30 ml) pH 7.0 and homogenised briefly at 0° C.

The pink mixture was then stirred at 0° C. for 3 hours the pH being maintained at 4° C. for 16 hours, sodium chloride (5.8 g) was dissolved in the suspension and the mixture was centrifuged at 25,000 g/0° C./1 hour. The resulting pink pellet weighed 4.0 g and was resuspended in 0.1 M sodium phosphate buffer pH 7.0 (20 ml).

Using 5% w/v penicillin G in 0.02 M sodium phosphate buffer pH 7.8 (20 ml) at 25° C., this suspension had a specific activity of $4.0 \times 10^{-5}$ moles/min/ml. This represents approximately 70% recovery of activity in the conjugate. The above suspension (4.0 ml) was mixed with 0.02 M sodium phosphate buffer (20 ml) and n-decanol (5 ml) and homogenised at c.4000 r.p.m. for 5 min. at 0° C. The emulsion was centrifuged at 100 g and room temperature for 20 min. and separated into an upper organic emulsion and a lower aqueous layer. The lower layer was retained and the upper was resuspended in 0.02 M sodium phosphate buffer (20 ml) and recentrifuged. The original lower layer contained a total activity of $1.25 \times 10^{-5}$ moles/min and the washed upper layer $9.5 \times 10^{-5}$ moles/min. The ratio of the specific activities (on a volume basis) is 21.6 (upper/lower). After determining the activity by the above method, the organic layer was recycled by gentle centrifugation and removal of the aqueous layer are shown in Table 5.

TABLE 5

Percentage initial activity of PAGAN119OD-n-decanol phase on successive flotation-reuse cycles.

| Cycle No. | % Activity | Cycle No. | % Activity |
|---|---|---|---|
| 1 | 80 | 7 | 46 |
| 2 | 86 | 8 | 46 |
| 3 | 93 | 9 | 44 |
| 4 | 73 | 10 | 42 |
| 5 | 64 | 11 | 45 |
| 6 | 47 | 12 | 43 |

EXAMPLE 12

Penicillin Acylase (n-Dodecylamino Gantrez AN 119)(PAGAN119DD)

n-Dodecylamino Gantrez AN 119 (0.25 g) was dissolved in dimethylformamide (1 ml) and added to a solution of penicillin acylase (c. 100 mg in 14 ml 0.1 M sodium phosphate buffer pH 7.0).

After brief homogenisation at 0° C. the suspension was stirred for 16 hours at 4° C. Ammonium sulphate (7.8 g) was added to the now homogeneous solution at 4° C., maintaining the pH at 7.0 with 1 M sodium carbonate solution. After solution of the ammonium sulphate, a cloudy suspension formed. This material was centrifuged at 25,000 g/0° C./1 hour. The pellet was resuspended in a solution of ammonium sulphate (7.8 g) in water (30 ml), pH 7.0 and recentrifuged. The final pellet weighed 1.36 g and was redissolved in water (10 ml) to give a viscous solution. The activity of the pellet (assay as above) was $1.62 \times 10^{-4}$ moles/min/gram wet weight representing an 80% activity recovery. The immobilisation of the water-soluble conjugate on n-decanol droplets is illustrated by the following experiment:

1 ml of the above solution was dissolved in 0.02 M sodium phosphate buffer (20 ml) and homogenised with n-decanol (10 ml) at 4000 r.p.m. for 3 min. at 0° C. The emulsion was separated into layers by centrifugation at 300 g for 10 min. The upper layer had a total activity of $1.14 \times 10^{-5}$ moles/min and its activity on successive recycles is shown in Table 6.

In a second experiment 2 ml of the enzyme conjugate solution was homogenised under the same conditions with n-decanol (2.5 ml) and 0.02 M sodium phosphate buffer (10 ml). After centrifugation and washing with 20 ml of the same buffer, the upper layer had an activity of $1.8 \times 10^{-5}$ moles/min and the original lower layer had an activity of $8.0 \times 10^{-6}$ moles/min. The ratio of specific activities (upper/lower, volume basis) is c.7.5.

TABLE 6

Percentage initial activity of PAGAN119DD-n-decanol phase on successive flotation-reuse cycles.

| Cycle No. | % Activity |
|---|---|
| 1 | 96 |
| 2 | 66 |
| 3 | 66 |
| 4 | 53 |

EXAMPLE 13

Trypsin (hydrolysed n-octadecylamino Gantrez AN 149) TGAN149DCMC

The swollen polymer gel (15 g) was mixed with 0.1 M sodium phosphate buffer pH 7.0 and adjusted to pH 4.7 with 2 N hydrochloric acid. 1-Cyclohexyl-3-(2-morpholinoethyl)carbodiimide metho-p-toluenesulphonate (CMC, 0.5 g) was added and the pH maintained at 4.7 with 2 N HCl, after 5 min at room temperature, bovine trypsin (75 mg in 0.1 M sodium phosphate buffer pH 7.0, 2 ml) was added and the pH of the mixture adjusted to 5.9 and maintained at this pH over the next 1 hour with 2 N sodium hydroxide. After 3 hours at room temperature, the gel was centrifuged 25,000 g/30 min/4° C. The pellet was resuspended in 0.1 M sodium phosphate buffer pH 7.0 (40 ml) and recentrifuged. The final pellet was mixed with the above buffer (15 ml) and n-decane (10 ml) and briefly homogenised. This procedure gave incomplete dispersion and the mixture was sonicated at 20 KH in 5×5 min bursts with intermittent cooling in ice. The final emulsion was centrifuged 100 g/15 min. The upper layer was washed three times with the phosphate buffer (25 ml). The final volume of the upper layer was 11 ml and the layer had an activity (assay as in Example 3) of 1050 BANA units/ml. Apparent activity recovery: c.5%.

EXAMPLE 14

(a) Hydrolysed n-octadecylamino Gantrez AN 119 hydrazide (GAN119ODH)

Gantrez AN 119 (5 g) was dissolved in dimethylformamide (20 ml) and warmed to 60° C. on a water bath. A solution of n-octadecylamine (2.8 g) in hot (80° C.) dimethylformamide (30 ml) was added and the mixture maintained at c.60° C. for 1 hour. After cooling to room temperature, the solution was added to a mixture of hydrazine hydrate (10 ml) and dimethylformamide (50 ml) at room temperature. A slight brown precipitate formed, and the mixture was stirred for 10 min. and water (500 ml) added. A soapy green solution resulted and, after stirring for 15 min. the pH was adjusted to 7.0 with conc. HCl and sodium chloride (50 g) added. Flocculation occurred and the suspension was centrifuged at 10,000 g/30 min/4° C. The pellet was resuspended in water (400 ml) and stirred 16 h at 4° C. then centrifuged as above to give a blue-grey pellet, (wet weight 39 g).

(b) Penicillin acylase (n-octadecylamino Gantrez AN 119)hydrazide coupled PAGAN119ODH GAN119ODH (5 g wet weight) was suspended in 2 N HCl (50 ml) and stirred at 0° C. for 15 min. A solution of sodium nitrite (0.5 g) in water (5 ml) was added and the mixture stirred at 0° C. for 10 min then centrifuged 25,000 g/30 min/0° C. and the pellet resuspended in 0.1 M sodium phosphate buffer pH 8.0 (50 ml) at 0° C. This suspension was added to a solution of penicillin acylase (100 ml containing 55 mg protein) and adjusted to pH 8.0. The suspension was stirred at 4° C. for 72 hours and then centrifuged 25,000 g/1 h/0° C., resuspended in 0.1 M sodium phosphate buffer pH 7.0 and recentrifuged. Final pellet weight: 3.74 g. Specific activity (assay as above): $5.2 \times 10^{-5}$ moles/min/gram. Activity recovery: 32.5%.

A suspension of the above conjugate in 0.1 M sodium phosphate buffer pH 7.0 (0.29 g/ml. 2.5 ml) was mixed with 0.02 m sodium phosphate buffer pH 7.8 (20 ml) and homogenised with n-decanol (7.5 ml) at 0° C. for 2 min and 5,000 r.p.m. centrifugation (100 g, 10 min) gave two layers. The lower layer had a total activity of $1.8 \times 10^{-6}$ moles/min and the upper layer after washing with the above buffer (20 ml) had an activity of $1.9 \times 10^{-5}$ moles/min. The ratio of specific activities (upper/lower, volume basis) is c.30. Recycle results with the upper phase are shown in Table 7.

TABLE 7

Percentage initial activity of PAGAN1190DH-n-decanol phase on successive flotation-reuse cycles.

| Cycle No. | % Activity |
|---|---|
| 1 | 90 |
| 2 | 84 |
| 3 | 74 |

EXAMPLE 15

Enzymatic cleavage of benzylpenicillin to produce 6-aminopenicllanic acid 1.0 g Gantrez AN 119 was dissolved in 10 ml. dimethyl formamide and 0.56 g. octadecylamine was added. The whole was stirred overnight at room temperature.

48 ml of a partially-purified preparation of penicillin acylase was adjusted to pH 9.0 with 1 M sodium carbonate solution. The solution of Gantrez resin was then added in two aliquots with homogenisation and a pH adjustment between the 2 additions. The mixture was then stirred for 3 hours, the pH being maintained at 9.0 by the addition of 1 M sodium hydroxide solution.

The enzyme-resin was then recovered by centrifugation resuspended in 120 ml 0.1 M phosphate buffer pH 7.0 and homogenised for 30 seconds. The enzyme-resin was recovered by centrifugation and the wash repeated.

20 g of enzyme-gel was homogenised with 80 ml n-decane and 20 ml 0.02 M phosphate buffer pH 7.8 for 1 min. The homogenate was added to 250 ml distilled water. The whole was warmed to 37°, adjusted to pH 7.8 and potassium benzyl penicillin (21.8 g) was added. The mixture was stirred for 5 hours and the pH was held at 7.8 by the addition of 4% (w/v) sodium hydroxide solution. At the end of the reaction the mixture was put into a separating funnel and the enzyme was allowed to separate from the aqueous phase. This took 30 min. The aqueous layer was then removed and 6-amino penicillanic was extracted in the following manner. The liquor was concentrated to ¼ volume, cooled to 5° and an equal volume of methyl isobutyl ketone was added with stirring. The pH was reduced to 4.3 by the addition of concentrated nitric acid whereupon the 6-aminopenicillanic acid was precipitated. The solid was recovered by filtration, washed with water and acetone and dried overnight at 40°.

7.65 g of 6-aminopenicillanic acid were obtained.

In the attached drawings, FIG. 1 represents the release of p-nitroaniline from N-α-benzoyl-DL-arginine-p-nitroanilide by:
  A. Trypsin (1mg)
  B. Trypsin complex TFODHG-1(0.1 g) of Example 6. FIG. 2 represents the release of p-nitrophenyl laurate catalyzed by:
  A. Lipase (0.1 g)
  B. Lipase complex LT2000 HDDG-1 (420 mg) of Example 7.

FIG. 3 is a schematic diagram of a reactor for carrying out the enzymatic process of the present invention.

I claim:

1. In an enzyme preparation having an enzyme portion and a polymeric support in which the enzyme portion is covalently bound directly to the polymeric support or is covalently bound to an inert bridging group which bridging group is in turn covalently bound to said polymeric support, the improvement which comprises the presence of a plurality of hydrophobic groups covalently bound to either or both of said enzyme portion and said polymeric support, said hydrophobic groups being hydrophobic at least by reason of a free terminal non-polar hydrocarbon portion of six or more carbon atoms, and being present in said enzyme preparation in such proportion as to impart, without deactivation of the enzyme portion, sufficient overall hydrophobic properties to said enzyme preparation to permit separation of the preparation from aqueous media through preferential association with an inert water-immiscible organic liquid.

2. An enzyme preparation according to claim 1 wherein the polymeric support is a polysaccharide material.

3. An enzyme preparation according to claim 2 wherein the polymeric support is dextran or sepharose.

4. An enzyme preparation according to claim 1 wherein the polymeric support is a copolymer of an oligosacccharide and epichlorhydrin.

5. An enzyme preparation according to claim 4 wherein the polymeric support is a copolymer of sucrose and epichlorhydrin.

6. An enzyme preparation according to claim 1 wherein the polymeric support comprises anhydride groups on the polymer backbone.

7. An enzyme preparation according to claim 6 wherein the polymeric support is a copolymer of methyl vinyl ether and maleic anhydride.

8. An enzyme preparation according to claim 1 wherein the enzyme of the enzyme portion is amylase, asparaginase neutral protease, alkaline protease, chymotrypsin, cellulase, dextranase, lipase, oxynitrilase, pepsin, penicillin acylase or trypsin.

9. An enzyme preparation according to claim 8 wherein the enzyme is penicillin acylase.

10. An enzyme preparation according to claim 1 wherein the non-polar groups are selected from the group consisting of alkyl of 6 to 30 carbon atoms, alkenyl of 6 to 50 carbon atoms, cycloalkyl of 6 to 20 carbon atoms, phenyl, unsubstituted or substituted with one to three alkyl groups of 1 to 3 carbon atoms, benzyl 2-phenethyl, 4-phenylbutyl and 2-tolyethyl.

11. An enzyme preparation according to claim 10 wherein the non-polar group is alkyl of 6 to 30 carbon atoms.

12. An enzyme preparation according to claim 11 wherein the non-polar group is n-decyl, n-dodecyl or n-octadecyl.

13. An enzyme preparation according to claim 1 wherein said inert bridging group is derived from an aliphatic $\alpha,\omega$-diamine of 2 to 10 carbon atoms, a water soluble dialdehyde or said diamine and said aldehyde.

14. An enzyme preparation according to claim 1 wherein the enzyme is linked directly to the polymeric support.

15. An enzyme preparation consisting essentially of an enzyme covalently bound directly to a plurality of hydrophobic groups, said hydrophobic groups being hydrophobic at least by reason of a free terminal non-polar hydrocarbon portion of six or more carbon atoms, and being present in said enzyme preparation in such proportion as to impart, without deactivation of the enzyme, sufficient overall hydrophobic properties to said enzyme preparation to permit separation of the preparation from aqueous media through preferential association with an inert water-immiscible organic liquid.

16. The process for the preparation of an enzyme preparation having an enzyme portion and a polymeric support in which the enzyme portion is covalently bound directly to the polymeric support or is covalently bound to an inert bridging group which bridging group is in turn covalently bound to said polymeric support said preparation further having a plurality of hydrophobic groups covalently bound to said polymeric support, said hydrophobic groups being hydrophobic at least by reason of a free terminal non-polar hydrocarbon portion of six or more carbon atoms, and being present in said enzyme preparation in such proportion as to impart, without deactivation of the enzyme portion, sufficient overall hydrophobic properties to said enzyme preparation to permit separation of the preparation from aqueous media through preferential association with an inert water-immiscible organic liquid, which process comprises chemically joining an enzyme or an activated derivative thereof (a) with a polymeric support having pendant functional groups capable of covalently reacting with said enzyme or activated derivative thereof and to which support has also been covalently bound said terminal hydrophobic groups or (b) with a polymeric support to which both said terminal hydrophobic groups and said bridging groups have been covalently bound, said bridging groups having terminal functional groups capable of covalently reacting with said enzyme or activated derivative thereof.

17. A process according to claim 16 wherein said polymeric support comprises pendant anhydride groups modified by the reaction with an amine of formula $R.NH_2$ or $R_2NH$ wherein R is non-polar hydrocarbon in an aprotic non-aqueous polar solvent.

18. A process according to claim 17 wherein the non-aqueous aprotic solvent is N,N-dimethylformamide.

19. A process according to claim 17 which is carried out in aqueous solution or suspension.

20. A process according to claim 19 which is carried out at a pH in the range pH 4 to pH 9.

21. In an enzymic reaction wherein an enzyme preparation is contacted, in aqueous medium, with a substrate for said enzyme, the enzyme preparation is separated from the reaction mixture and the reaction product is recovered, the improvement permitting re-use of the separated enzyme preparation which comprises utilizing an enzyme preparation having an enzyme portion, a polymeric support said enzyme portion being covalently bound directly to the polymeric support or covalently bound to an inert bridging group which bridging group is in turn covalently bound to said polymeric support, and a plurality of hydrophobic groups covalently bound to either or both of said enzyme portion and said polymeric support, said hydrophobic groups being hydrophobic at least by reason of a free terminal non-polar hydrocarbon portion of six or more carbon atoms, and being present in said enzyme preparation in such proportion as to impart, without deactivation of the enzyme portion, sufficient overall hydrophobic properties to said enzyme preparation to permit separation of the preparation from aqueous media through preferential association with an inert water-immiscible organic liquid.

22. A process according to claim 21 wherein the inert water-immiscible organic liquid is an alkane, an aromatic hydrocarbon, a higher aliphatic ester, or an aliphatic alcohol of 2 to 14 carbon atoms.

23. A process according to claim 21 wherein contact between said enzyme preparation and said inert water-immiscible liquid is established by agitation.

24. A process according to claim 23 wherein the contact between said enzyme preparation and said water-immiscible liquid is established prior to said enzymic reaction.

25. A process according to claim 21 wherein said enzyme is penicillin acylase.

26. A process according to claim 25 wherein the substrate is benzylpenicillin or phenoxymethylpenicillin.

27. A process for the preparation of 6-amino-penicillanic acid from benzylpenicillin, which process comprises contacting benzylpenicillin in aqueous medium with an inert water-immiscible organic liquid and an enzyme preparation comprising penicillin acylase covalently attached to a plurality of free terminal non-polar groups in such proportion as to impart to the preparation sufficient overall hydrophobic properties to cause preferential association with said inert water-immiscible organic liquid, thereafter allowing the aqueous and water-immiscible layers to separate, separating said water-immiscible layer and the associated enzyme preparation from the aqueous reaction mixture, and recovering the 6-aminopenicillanic acid from the aqueous layer.

* * * * *